United States Patent
Nelson

(10) Patent No.: US 7,636,419 B1
(45) Date of Patent: Dec. 22, 2009

(54) METHOD AND APPARATUS FOR AUTOMATED THREE DIMENSIONAL DOSIMETRY

(76) Inventor: Brett Kilgore Nelson, 100 Royal Oak Ct., Scotts Valley, CA (US) 95066

(*) Notice: Subject to any disclaimer, the term of this patent is extended or adjusted under 35 U.S.C. 154(b) by 207 days.

(21) Appl. No.: 11/708,936

(22) Filed: Feb. 20, 2007

Related U.S. Application Data

(60) Provisional application No. 60/775,618, filed on Feb. 21, 2006.

(51) Int. Cl.
*A61N 5/10* (2006.01)
*G01T 1/20* (2006.01)

(52) U.S. Cl. .................. 378/65; 250/363.01

(58) Field of Classification Search .......... 378/65, 378/210; 250/484.5, 363.01
See application file for complete search history.

(56) References Cited

U.S. PATENT DOCUMENTS

| | | | |
|---|---|---|---|
| 4,931,653 A | 6/1990 | Hamm et al. | |
| 5,006,714 A | 4/1991 | Attix | |
| 5,821,541 A * | 10/1998 | Tumer | 250/370.09 |
| 6,345,114 B1 | 2/2002 | Mackie et al. | |
| 6,904,162 B2 | 6/2005 | Robar et al. | |
| 6,998,604 B2 | 2/2006 | Nishizawa et al. | |
| 7,345,284 B2 | 3/2008 | Tumer | |

OTHER PUBLICATIONS

Binns, et al., Bevalac Calibration of the Sofie Range and Hodoscope Detectors, Aug. 1985, Nasa—Goddards Space Flight Center 19th Intern. Cosmis Ray Conf., vol. 3, pp. 272-275.*

Hink et al., The ACE-CRIS Scintillating Optical Fiber (SOFT) detector: a calibration at the NSCL, 1996, SPIE vol. 2806, pp. 199-208.*
Stieber, V.W., "Gamma Knife vs. Linear Accelerator Radiosurgery," Technology in Cancer Research and Treatment, Apr. 2003, vol. 2, No. 2, ISSN 1533-0346.
Tyrell, G.C., "UV-Shifted Silicon Devices for Imaging and Detection," Fig. 4, Photonics Spectra, Sep. 2006.

* cited by examiner

*Primary Examiner*—Edward J Glick
*Assistant Examiner*—Anastasia Midkiff

(57) ABSTRACT

A system and method for recording in real-time the duration, strength, and position of multiple collimated beams of ionizing radiation as delivered during stereotactic radiosurgery for the purpose calibrating the radiological system and verifying the treatment plans for various lesions. The beams of ionizing radiation are made visible by means of a cone or paraboloid shaped scintillator the interior of which is viewed by a sensitive visible-light camera equipped with fish-eye style optics mounted in a darkened enclosure. As the beam enters and exits the scintillator cone, two bright spots are seen in the camera's field of view. The centroids of these spots create a hodoscope and describe the path of the beam through three dimensional space. A computer connected to the camera measures the location and intensity of these spots over time during radiosurgery, calculates each beam path, and archives the spot parameters and computed beam paths to memory. Software algorithms reconstruct a mathematical description of each treatment beam that intersects the scintillator volume. In turn, these rays are used to construct a three dimensional model of the dosimetric pattern delivered within the scintillator. The operator can then determine discrepancies between the measured dosimetric pattern and the intended radiosurgery treatment or calibration pattern.

10 Claims, 5 Drawing Sheets

METHOD AND APPARATUS FOR AUTOMATED THREE DIMENSIONAL DOSIMETRY

Provisional Patent Filed: Feb. 21, 2006 Ser. No. 60/775,618

FIELD OF THE INVENTION

This invention relates to the automated electronic measurement of three dimensional dosimetric patterns created by intersecting beams of ionizing radiation as sequentially delivered from a stereotactic radiology system.

BACKGROUND OF THE INVENTION

Stereotactic radiosurgery is becoming a popular treatment modality for cancers and other lesions that are untreatable by conventional chemotherapy, surgical, and intensity modulated radiation therapies. In stereotactic radiosurgery, many individual collimated beams of ionizing radiation are passed through the tumor from as many different directions as needed to conformally irradiate the entire tumor volume and thus render it inert. These beams of radiation range from X-ray to Gamma ray in wavelength and are typically generated using linear accelerators or radioisotopes.

In order to position the radiation beams for successful treatment of the patient, these radiosurgery systems require large mechanisms capable of moving the radiation source through precise locations and angles around the patient. The challenge then arises of how to match the coordinate system of the radiosurgery apparatus with the location of the patient's lesion as he or she reclines upon the treatment couch. In addition, it would be desirable to verify that the treatment plan approved by the radiologist and delivered by radiosurgery sufficiently conforms to the shape of the tumor. Traditionally, X-ray film has been used to solve both of these problems. U.S. Pat. No. 6,904,162 describes a film based 3D dose measurement technique that uses many individual pieces of film loaded into a cassettebox that is then fitted into an enclosure that disperses radiation in a similar way as human tissue. This enclosure is referred to as a phantom and may take the form of a human head or torso. After the phantom has been exposed, the individual layers of film are manually removed, digitized with a scanner, and then computer assembled into a 3D dosimetric representation of the treated volume using laminography algorithms.

There are several problems with X-ray film laminography. The first is that the process of manually loading and unloading the cassettebox and then scanning the film is tedious for the technician and introduces alignment errors. The second is that X-ray film has a different sensitivity to radiation exposure as does human tissue. The third is that different lots of X-ray film may have a range of sensitivities because of variations during the manufacturing process. A superior approach would require a minimum of technician time occupied in the process of creating the dose map. It would also be desirable to generate a dose map as soon as the radiosurgery is completed. Other positive goals would be to capture the radiation in a uniform way from treatment to treatment and then reconstruct the radiation dose in such a way as to more closely mimic the characteristics of human tissue.

One technique that partially fulfills these requirements is the dosimetry probe described in U.S. Pat. No. 5,006,714. In this apparatus, the visible light created when ionizing radiation strikes a scintillator material is used to measure the radiation dose given to a single point in 3D space. Unfortunately, the probe must be moved about in an XYZ fashion to sample additional spatial points rendering the technique unusable for real-time three dimensional dosimetry. A more promising approach is described in U.S. Pat. No. 6,998,604 where a thin slice of scintillator material is used to generate a two dimensional representation of the incident radiation. In order to build up a third dimension of dose information, the scintillator must be moved between samples again rendering it unusable for general purpose real-time stereotactic radiosurgery dosimetry.

U.S. Pat. No. 4,931,653 describes a system that can generate true three-dimensional information from incident radiation in real-time. In this system, the radiation enters a chamber filled with gas which is subjected to an electric field. As the gas ionizes along the beam path, a system of four cameras capture the beam path in sufficient detail to completely describe the beam's path through the chamber. Once a beam is detected, the electric field must be collapsed and then restored in order to prevent the ionization of the entire chamber. The large number of optical paths for the cameras and the fact the beam must pass through a medium that does not resemble human tissue (e.g. metallic conductors) make this approach unsatisfactory for integration within a radiosurgery phantom.

BACKGROUND OF THE INVENTION

Objects and Advantages

A popular design in high energy physics for extracting three-dimensional information from incident radiation is the hodoscope. If the entrance and exit points of a linear radiation beam are known, then all of the points between them where the beam passes are also known (see U.S. Pat. Application 20060208196). The entrance and exit points can be detected by using solid-state XY detectors or various types of scintillators connected to photomultiplier tubes and digitizing electronics.

The present invention described is unique in that it uses a fish-eye style lens system so that only one camera is necessary to view the beam entrance and exit points as it travels through a scintillator chamber that is either conic or paraboloid in shape. In the preferred embodiment of this invention the scintillator is a cone because of the relative ease of fabrication and the simplified mathematics needed to describe its operation. The hollow nature of the scintillator and the single optical path make the design suitable for convenient integration and use with a variety of radiosurgery phantoms.

The present invention also takes advantage of the latest gadolinium oxysulfide (GOS) scintillator phosphors so that the requirements for viewing Gamma ray beams are well within the capabilities of existing commercial CCD cameras. The fact that only one CCD camera is needed for beam measurements reduces the bill of materials and lowers the cost for a complete dosimetric system making the system more price competitive with film based dosimeters.

The present invention makes use of a computer to not only produce 3D measurements of the ionizing radiation but also to automate the capture and reconstruction process. The technician interacts with the software mainly to start and stop it thereby lowering the overall cost of use. Once the radiosurgery is completed, the dosimetric pattern is ready to be viewed or exported to other software applications.

SUMMARY OF THE INVENTION

The present invention features a darkened enclosure that contains a CCD camera attached to a C-mount lens system that is focused on the front surface of a ball lens. The ball lens is positioned at the open end of a cone such that the entire interior of the cone is seen wide angle fish-eye style in the camera's field of view. The inside of the cone is coated with scintillator phosphor that is capable of fluorescing with visible light when struck with ionizing radiation. When a Gamma ray as delivered by a stereotactic radiosurgery system intersects the volume of the cone, the camera sees two bright spots corresponding to the entry and exit points of the beam. A computer connected to the camera can calculate the centroids of the beam entry and exit spots and algorithmically determine the XYZ coordinates of each in relation to a reference point along the axis of the cone called the isocenter. The cone is designed to fit within a variety of head and torso shaped phantoms. The enclosure, cone, phantom, and computer comprise the dosimeter apparatus of the invention.

There are many methods by which the dosimeter apparatus may be used to make three dimensional beam dose measurements. The preferred embodiment described here is a software program that continually monitors the beam entry and exit points during a stereotactic radiosurgery treatment. As each beam is detected and measured, the XYZ coordinates of the entry and exit points are used to simulate the delivered dose along a path through a three dimensional array of pixels (or voxels) in computer memory. The value in each voxel is advanced from an initial value of zero according to the beam energy profile and the distance from the voxel to the beam. Once the treatment is completed, the entire array of voxels may be saved to disk in DICOM 3.0 format or viewed slice by slice along the Z axis of the array.

BRIEF DESCRIPTION OF THE DRAWINGS

While the specification concludes with claims particularly pointing out and distinctly claiming the present invention, objects and advantages of the invention can be more readily ascertained from the following description of a preferred embodiment when used in conjunction with the accompanying drawings in which:

DETAILED DESCRIPTION OF THE INVENTION

Figure 1:
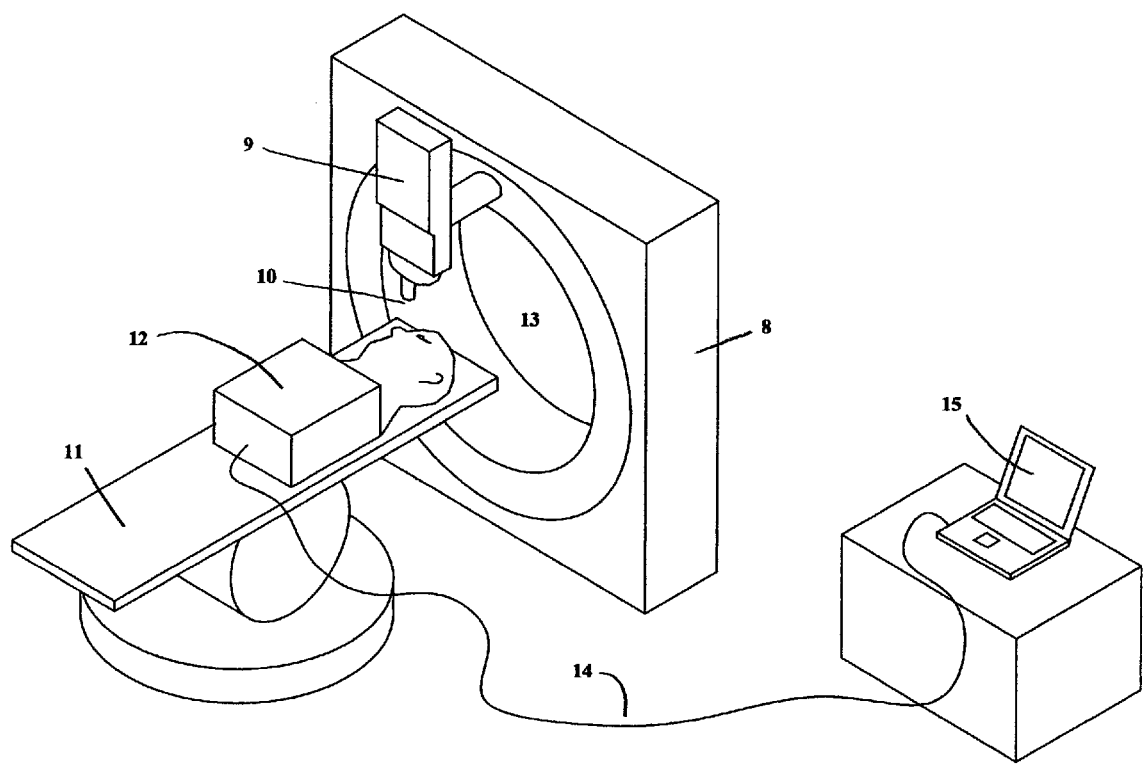
FIG. 1 is a perspective view of a linear accelerator radiology system with the present invention occupying the place of the patient providing camera images of the treatment beam to the attached laptop computer for analysis and three dimensional dose reconstruction.
Figure 2:
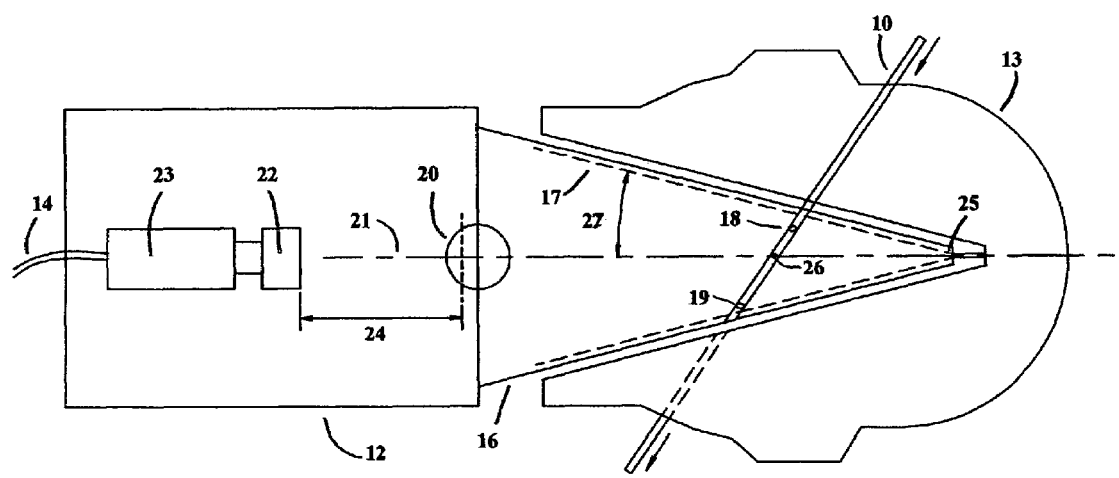
FIG. 2 is a cross-section of the camera, optics, and scintillator portion of the invention with the treatment beam passing through the scintillator cone illuminating the entry and exit points on the interior side of the cone. The outline of a head-shaped phantom is shown fitting around the outside of the scintillator cone.

Referring now to FIGS. 1, 2, 3, 4, and 5, a stereotactic radiosurgery system 8, suitable for the present invention, includes a linear accelerator 9 or radioactive isotope (not shown) radiation source producing a narrow beam 10 across or through the treatment couch 11 that may hold the patient (not shown) or automated dosimeter enclosure 12 with attached head phantom 13. The radiation beam may be in the Gamma ray wavelengths of 1-10 MEV and collimated to be approximately 5 mm in effective treatment diameter. A cable 14 transfers images from the dosimeter enclosure 12 to the computer 15 which interprets the images into a three dimensional dose pattern.

The radiation beam 10 passes through the phantom 13 and enters the imaging cone 16 section of the dosimeter fluorescing the interior scintillator coating 17 at the entry 18 and exit 19 points forming a hodoscope that defines the entire path of the beam 10. Scintillating phosphors made up of gadolinium oxysulfides (GOS) doped with the lanthanide elements have been found to work well with linear accelerator beam energies of 6 MEV. The visible light photons from these two points 18 19 pass through the ball lens 20 and on through a traditional C-mount lens 22 attached to camera 23 that has a threshold of sensitivity of 0.01 lux or better. The camera 23 and C-mount lens 22 are positioned such that the focal length 24 to the ball lens 20 maximizes the amount of scintillator 17 that is visible and in focus. The camera 23 is also positioned along axis 21 so that the vertex 25 of the scintillator cone 17 is at the center of the field of view. The cable 14 transfers a stream of scintillator 17 images from camera 23 to the dosimeter computer 15. A point is chosen within the dosimeter cone 16 to be the isocenter 26 of the dosimeter and serves as the origin for the Cartesian coordinate system used in analyzing the scintillator 17 images and calculating the XYZ values for the hodoscope beam spots 18 19. The cone angle 27 is also used in these calculations. The beam 10 is shown passing through the isocenter for the convenience of explaining the mathematical relationship between the camera and cone coordinate systems. During a given treatment plan, many beams of radiation will pass near but not through the isocenter.

Figure 3:
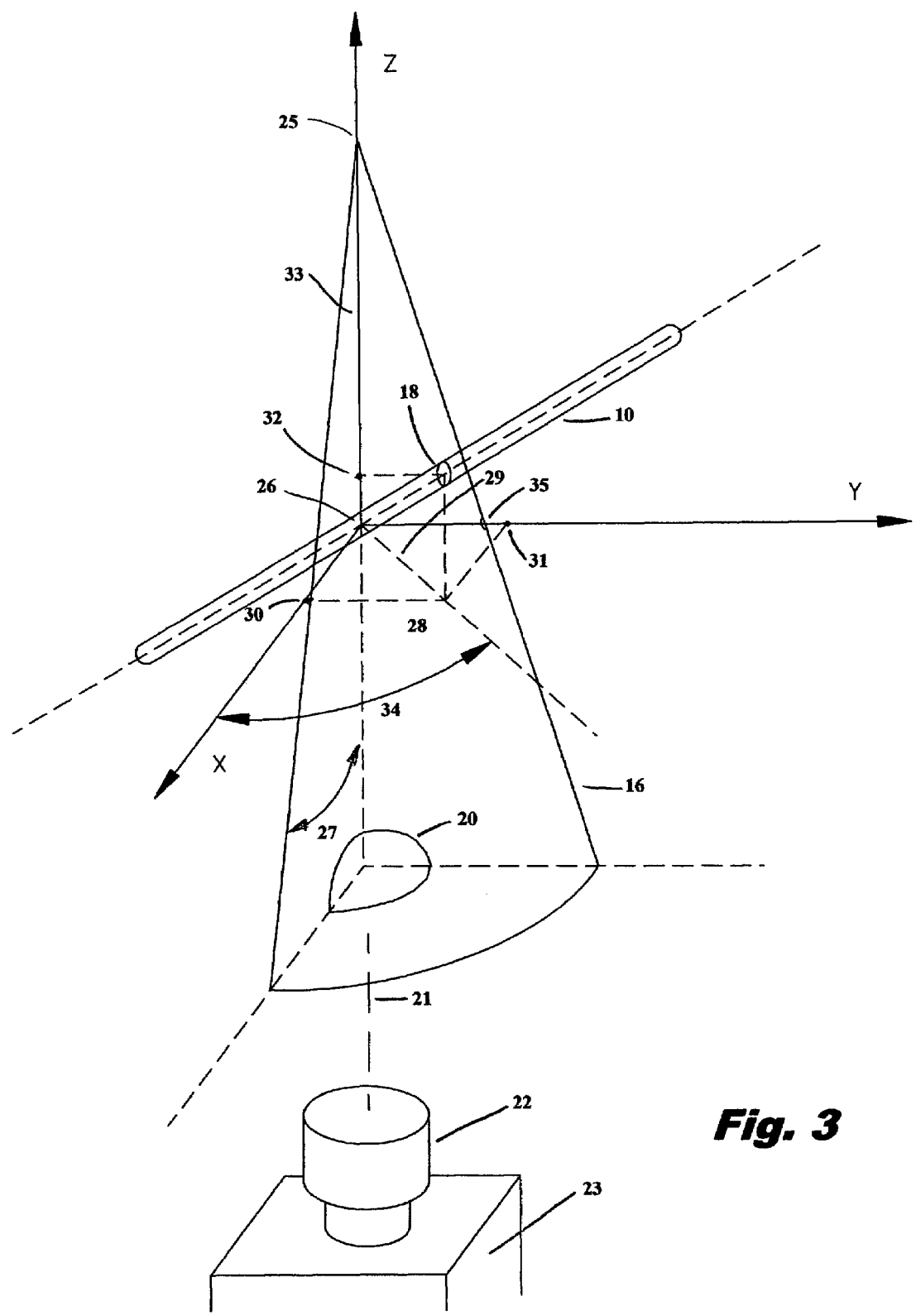
FIG. 3 is a single quadrant view of the scintillator cone and treatment beam showing the mathematical relationship of the cone coordinate system and how it relates to the field of view of the camera.

Referring now to FIG. 3, the first quadrant of the imaging cone 16 interior is depicted with the origin of the Cartesian coordinate system being the isocenter 26. The beam 10 entry point 18 to the imaging cone is shown projected down on to the isocenter's XY plane at 28. The distance from 28 to the isocenter is called 29. The X coordinate of the beam entry point is shown at 30, the Y coordinate at 31, and the Z coordinate at 32. The distance from the vertex 25 of the imaging cone 16 to the beam's Z coordinate 32 is 33. The angle from the X axis to the ray that starts at the isocenter 22 and travels through 28 is called 34. The viewing orientation of the camera 23 can be seen directly below the ball lens 20 looking up along the Z axis. The intersection of the imaging cone and the Y axis at 35 is a useful reference point to help understand how the Cartesian coordinates map into the camera's 23 field of view as shown in FIG. 4.

Figure 4:
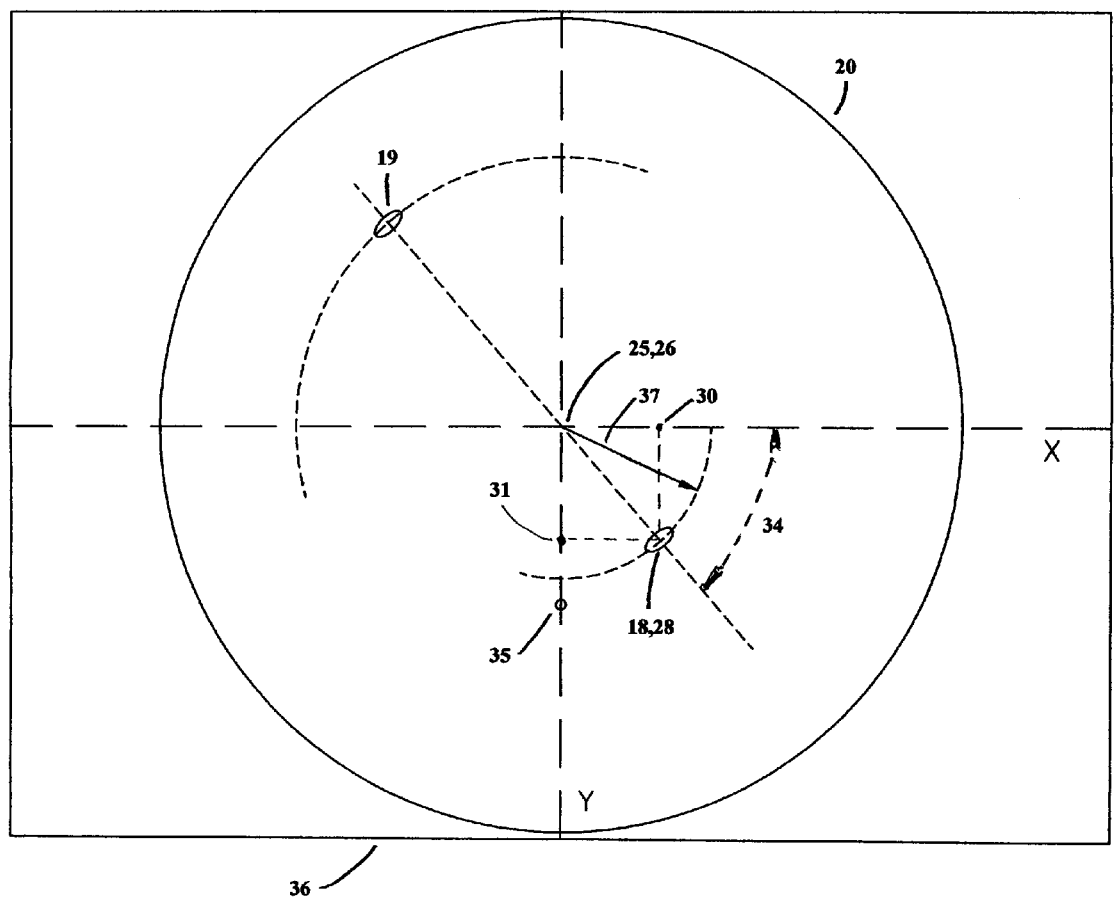
FIG. 4 shows the fish-eye style camera view of the interior of the scintillator cone, the entry and exit spots of the treatment beam, and how the cone coordinate system corresponds to the bitmap produced by the camera.

Referring now to FIG. 4, camera 23 produces a pixel bitmap 36 where the Y axis of the Cartesian coordinate system based on the isocenter 26 is inverted by the ball lens 20 and appears at the bottom of the camera's 23 field of view. The X axis is also inverted and appears on the right side of the bitmap 36. The Z axis, isocenter 26, and imaging cone vertex 25 are collapsed to a single point at the center of the bitmap 36. In reality, the typical bitmap image from the camera is mostly black or dark gray monochrome pixels. The beam entry 18 and exit 19 points created by the fluorescing action of the Gamma ray beam on the phosphor compounds in the scintillator material are the only brighter regions on the entire image. The angle 34 can be measured by finding the XY centroid 28 of the entry 18 grayscale region, calculating the delta x and delta y distances from the bitmap center 25, and finding the arctangent of delta y divided by delta x. This same XY centroid can also be used to determine the bitmap radius 37 value by taking the square root of the sum of the squares of this same delta y and delta x.

The 3D Z coordinate 32 of the beam entry point 18 is a function of this radius value 37. When the radius value is 0, the Z coordinate 32 is at the imaging cone vertex 25. The Z coordinate value 32 monotonically decreases as 37 increases in size and goes negative as the radius value becomes larger than the Y coordinate of 35. This transfer function is roughly linear when 37 is small, but because of the complex nature of the ball lens optics, a piece-wise linear approximation is used to compute the transfer function that converts the radius 37 measurement to the 3D Z coordinate 32. The coefficients of this transfer function are obtained from a test fixture during the fabrication of each dosimeter after the camera 23 is mounted and aligned with the imaging cone 16.

Once the 3D Z coordinate 32 has been calculated, the imaging cone projection radius 29 can be determined knowing that 29 divided by the distance from the cone vertex 25 minus the Z coordinate 32 is equal to the tangent of the cone angle 27. The 3D X coordinate then becomes radius 29 times the cosine of angle 34. Similarly, the 3D Y coordinate is the radius 29 times the sine of angle 34.

Figure 5:
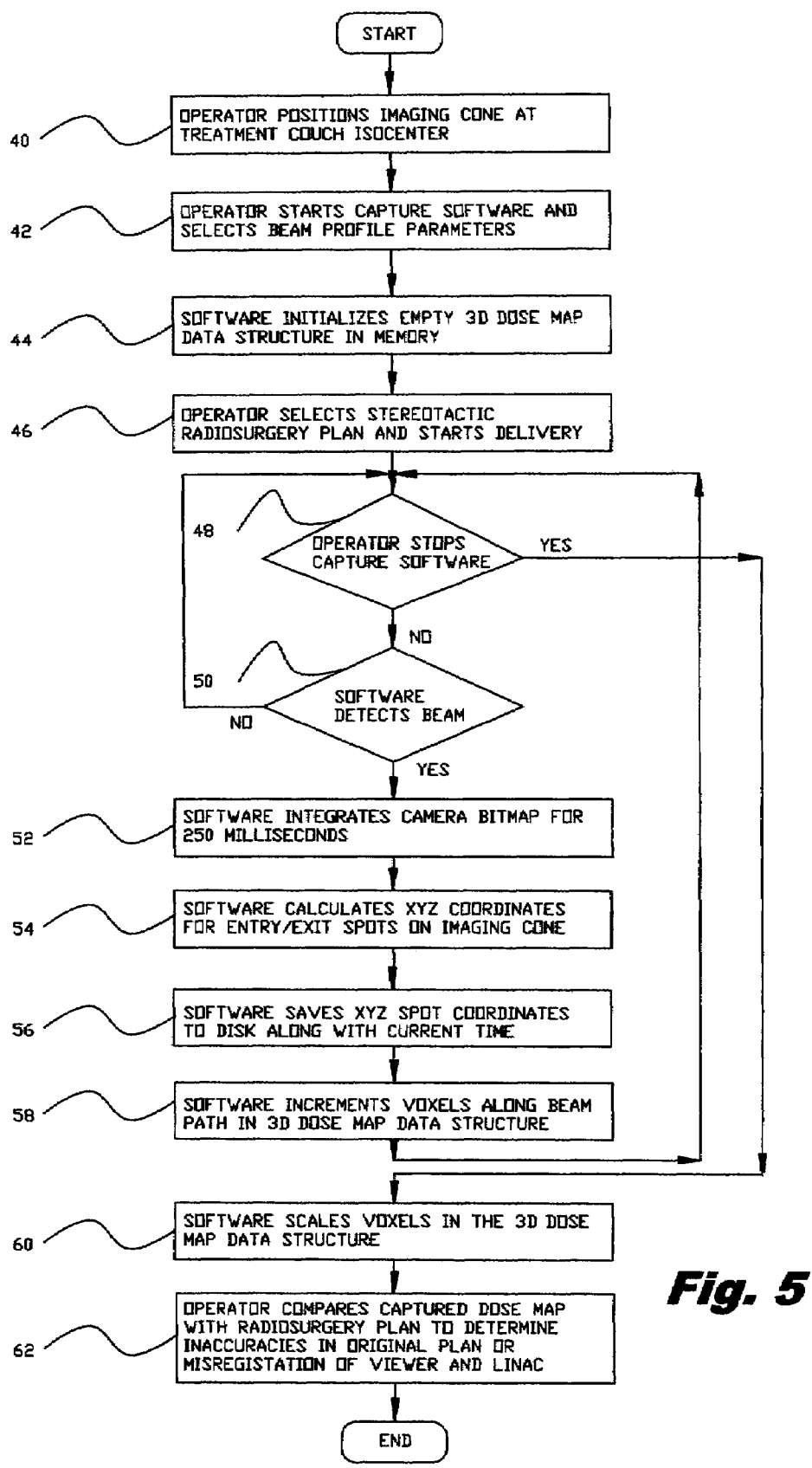
FIG. 5 is a flowchart that shows the major steps involved in capturing a treatment plan as delivered during radiosurgery and constructing the delivered dose pattern in computer memory.

Referring now also to FIG. 5, the first step of the method for this invention, represented by process block 40, is to position the imaging cone isocenter at the known isocenter of the treatment couch. The dimensions of dosimeter enclosure 12 are known in their relation to the dosimeter isocenter and may be used for precise positioning of the apparatus. Once positioned, the phantom 13 is slipped over the imaging cone 14. It is always the goal of stereotactic radiosurgery systems that the linear accelerator isocenter be calibrated and adjusted to coincide with the treatment couch isocenter.

At process block 42 the dosimeter software is started using the computer 15 and the expected beam energy profile is selected. Linear accelerator radiosurgery systems typically have a variety of beam collimators, one of which is manually installed on the system before a treatment begins. Each beam collimator produces a different beam diameter with a distinctive energy profile. This energy profile may have been determined externally to the software by a different piece of equipment and entered by disk file, or generated at an earlier time using the present invention. The process of measuring a beam profile with the present invention involves integrating beam images for several seconds utilizing a beam that passes through the dosimeter isocenter and reference point 35 resulting in two horizontal streaks in the resulting camera bitmap. The grayscale values of a horizontal path through the resulting beam spots can be used to calculate the relative spatial beam energy on entry and exit of the imaging cone. The relative grayscale value at each pixel is proportional to the base 10 logarithm of the beam energy when using GOS phosphors.

At process block 44 the dosimeter software initializes an empty three dimensional dose map within computer memory. The array of voxels within this data structure has a center point that corresponds to the isocenter of the imaging cone. The dosimeter software then enters a loop at decision block 48 waiting for the beam to become visible within the imaging cone.

At process block 46 the operator selects and starts the delivery of the stereotactic radiosurgery plan. The intended center of the collective dose pattern must be positioned within imaging cone 14 near the isocenter of the dosimeter.

At decision block 48 the dosimeter software checks for an operator abort signal from the computer user interface. Since the radiosurgery treatments may last more than an hour, it is reasonable for the software to continuously wait for beam treatments until halted by the operator. Other variations of the software might automatically exit if no beam activity has been detected within a certain time limit. An exit command causes the dosimeter software to jump to process block 60.

At decision block 50 the software monitors the image data flowing from the camera and checks for the presence of enough lighter areas in the mostly dark gray bitmap to signify that a beam is passing through the imaging cone 14. The frame rate of the camera is typically 60 frames per second and so beam detection by the software typically lags the real beam delivery by about 16 milliseconds.

At process block 52 the bitmap data from the camera is integrated and averaged over 250 milliseconds so that there is sufficient data to remove noise and enhance the position of the hodoscope entry and exit beam spots. This sampling period corresponds to about 16 frames of bitmap data from the camera and is the approximate length of time the scintillator phosphors remain lit after being exposed to a single pulse of gamma radiation as produced by a 6 MEV linear accelerator with a 5 microsecond pulse duration. This 250 millisecond sampling period determines how quickly the dosimeter can recognize distinct beam treatments. Since the radiosurgery apparatus must physically move between treatments, the software can easily keep up with traditional treatment plans as delivered by the current generation of radiosurgery hardware. Some treatment plans deliver doses while the linear accelerator moves in an arc sweeping the beam through the lesion. In these cases, the dosimeter sampling rate of 4 captures per second approximates the delivered dose.

At process block 54 the XYZ positions of the hodoscope entry and exit beam spots are derived from the integrated bitmap data.

At process block 56 the three dimensional coordinates of the hodoscope entry and exit beam spots are saved to disk along with the current time.

At process block 58 the entry and exit beam coordinates are used along with the beam profile data to simulate the beam dose path in the three dimensional dose map located in computer memory. Each new beam dose causes existing numeric voxel values to increment along that corresponding beam path in the three dimensional bitmap data structure. In this way, a given voxel value will increase each time a beam passes through it. The amount each voxel is incremented is determined by the beam profile data selected by the operator at process block 42 and the distance from the voxel to the beam. Modern multi-core computer hardware and multi-threaded programming techniques allow these computations to take place as the next treatment beam is being captured and integrated. A related software program could be created to process all the beam measurements after treatment has been completed. This would allow a more lengthy and detailed analysis of the beam paths for higher resolution dose reconstruction. Different beam profiles representing different style collimators could be used as input for this program as a means of trying alternative dosimetric patterns to optimize a given treatment plan. After the completion of process block 58, control is transferred back to decision block 48 and so the dosimeter software will stay in a loop until the operator enters an exit command via the user interface. An exit command transfers control to process block 60.

At process block 60, final computations are made to the three dimensional dose map so that the values in memory represent a range (typically 0-255) that can be easily output to disk as a DICOM format file or viewed on the computer monitor.

At process block 62 the captured three dimensional dose map made by the dosimeter can now be compared with the lesion treatment volume described by the radiosurgery plan. In particular, the isocenters of the two volumes can be compared in order to correct any misregistration between the linear accelerator and treatment couch coordinate systems.

While the invention has been particularly shown and described with reference to a preferred embodiment thereof, it will be understood by those skilled in the art that various changes in form and details may be made without departing from the spirit and scope of the invention.

What is claimed is:

1. A hodoscope dosimeter comprising a tapered scintillator volume that flashes light in two places when struck by an ionizing radiation beam from a stereotactic radiosurgery system, a camera that records an image of said light, and a computer that calculates location coordinates of said beam and that also calculates a profile of said beam, including its width and intensity.

2. The hodoscope dosimeter of claim 1 further comprising a housing that makes it interchangeable with a variety of radiosurgery phantoms.

3. The hodoscope dosimeter of claim 1 where said scintillator has a conical shape, and where said two places are the entry and exit points of said beam striking and leaving said conical shape.

4. A hodoscope dosimeter comprising a tapered scintillator volume that flashes light in two places when struck by an ionizing radiation beam from a stereotactic radiosurgery system that moves said beam in different directions, a camera that records an image of said light, and a computer that calculates location coordinates of said beam and that records said location coordinates in real time.

5. A method for calibrating a stereotactic radiosurgery system, comprising detecting an X-ray or Gamma ray beam by letting it intersect a tapered scintillator volume twice, capturing an optical image of light flashes from said scintillator, computing three dimensional location coordinates for said beam, and computing a profile of said beam, including its width and intensity.

6. The method of claim 5 further comprising monitoring beam movements as delivered by a radiosurgery system and reporting said three dimensional location coordinates of said beams in real time.

7. The method of claim 6 further comprising computing a delivered three dimensional dose volume using the location coordinates and profiles of said beams as they change intensity and direction.

8. The method of claim 7 further comprising displaying said three dimensional dose volume on a computer display.

9. The method of claim 7 further comprising saving said three dimensional dose volume to a computer file in a standard format.

10. The method of claim 7 further comprising recalculating said three dimensional dose volume by using different beam positions and profiles for the purpose of more closely matching said three dimensional dose volume to the intended dose volume.

* * * * *